United States Patent
Qiang et al.

(10) Patent No.: US 10,208,077 B1
(45) Date of Patent: Feb. 19, 2019

(54) AESCULIN LIPOIC ACID ESTER WITH ANTIOXIDANT ACTIVITY AND A METHOD OF PREPARING THE SAME

(71) Applicants: Taotao Qiang, Xi'an (CN); Yunying Song, Xi'an (CN); Longfang Ren, Xi'an (CN); Xuechuang Wang, Xi'an (CN); Chengyuan Liang, Xi'an (CN); Lei Tian, Xi'an (CN); Xinke Ju, Xi'an (CN); Han Li, Xi'an (CN); Qianqian Zhao, Xi'an (CN)

(72) Inventors: Taotao Qiang, Xi'an (CN); Yunying Song, Xi'an (CN); Longfang Ren, Xi'an (CN); Xuechuang Wang, Xi'an (CN); Chengyuan Liang, Xi'an (CN); Lei Tian, Xi'an (CN); Xinke Ju, Xi'an (CN); Han Li, Xi'an (CN); Qianqian Zhao, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 0 days.

(21) Appl. No.: 16/101,412

(22) Filed: Aug. 11, 2018

(51) Int. Cl.
*C07H 17/075* (2006.01)

(52) U.S. Cl.
CPC .................................. *C07H 17/075* (2013.01)

(58) Field of Classification Search
None
See application file for complete search history.

(56) References Cited

FOREIGN PATENT DOCUMENTS

KR          101329219 B1  *  11/2013

* cited by examiner

*Primary Examiner* — Traviss C McIntosh, III
(74) *Attorney, Agent, or Firm* — SZDC Law P.C.

(57) ABSTRACT

A compound having the formula I:

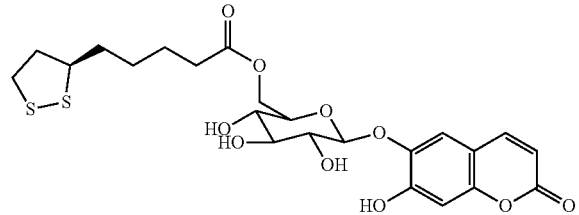

is disclosed. A method of preparing the compound of formula I is also disclosed.

10 Claims, 1 Drawing Sheet

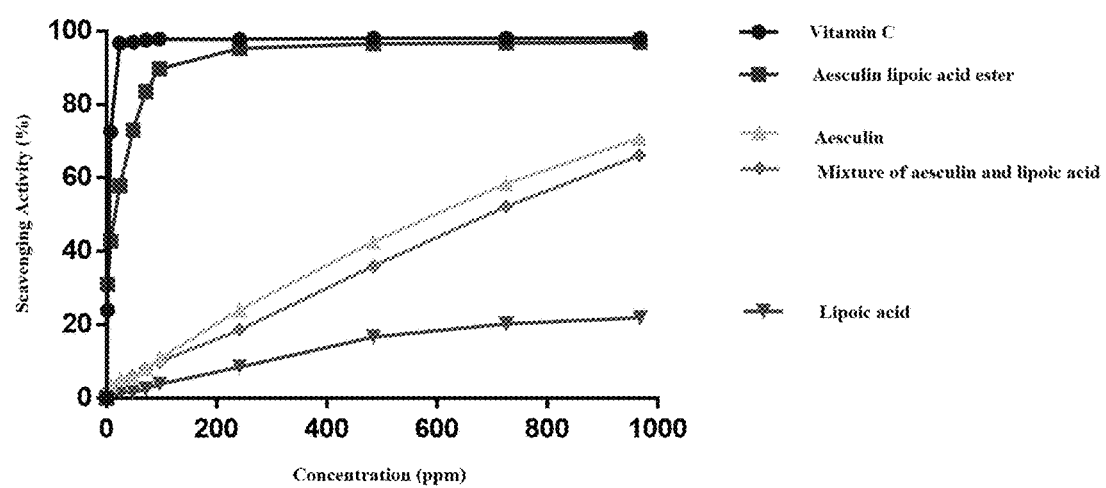

AESCULIN LIPOIC ACID ESTER WITH ANTIOXIDANT ACTIVITY AND A METHOD OF PREPARING THE SAME

The present invention claims priority to Chinese Patent Application No. CN 201810649366.X, filed on Jun. 22, 2018, which is incorporated by reference for all purposes as if fully set forth herein.

FIELD OF THE INVENTION

The present invention relates to food and cosmetic additives, in particular, to an aesculin lipoic acid ester having antioxidant activity and a method of preparing the same.

BACKGROUND OF THE INVENTION

Due to the technological advancement of the food additive industry, the development, production, and application of food antioxidants have been greatly advanced. Antioxidant is an important food additive. It is mainly used to prevent or delay the automatic oxidation of the oil in the food. It also prevents nutrient damage, browning and fading due to oxidation during storage. At the same time, in recent years, studies have found that human skin will age due to oxidation and ultraviolet radiation, so more and more antioxidants are also used in the cosmetics industry. More research work has been conducted to develop new antioxidants. Synthetic and semi-synthetic antioxidants have attracted more and more attentions.

Aesculin (compound of formula II) is coumarin compound extracted from the dry bark or dry skin of the olein tree of the genus *Oleaceae*, and the effective component of Chinese traditional medicine, Qinpi (Cortex Fraxini). Aesculin has anti-inflammatory, antibacterial, diuretic and anti-tumor effects. There is no report on the use of aesculin as antioxidant.

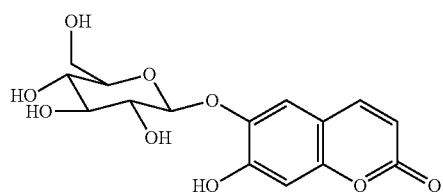

II

Lipoic acid (also known as α-lipoic acid and alpha lipoic acid; compound of formula III) is a coenzyme present in mitochondria, similar to vitamins, and eliminates free radicals that accelerate aging and disease. Lipoic acid enters the cells after being absorbed into the intestines in the body. It has both fat-soluble and water-soluble properties. It is used in the treatment and prevention of various diseases such as heart disease and diabetes. It is believed to preserve and regenerate other antioxidants, such as vitamins C and E.

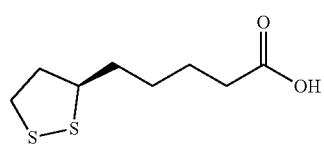

III

SUMMARY OF THE INVENTION

In one embodiment, the present invention provides a compound having the following formula I (an aesculin lipoic acid ester):

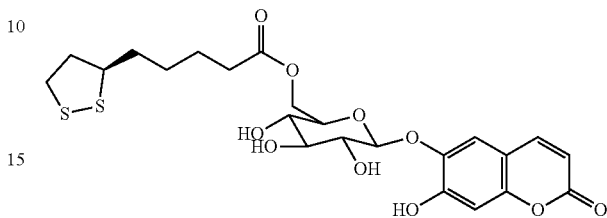

I

In one embodiment, the present invention provides a method of preparing the compound of formula I. The method includes reacting the compound of formula II with the compound of formula III to obtain the compound of formula I:

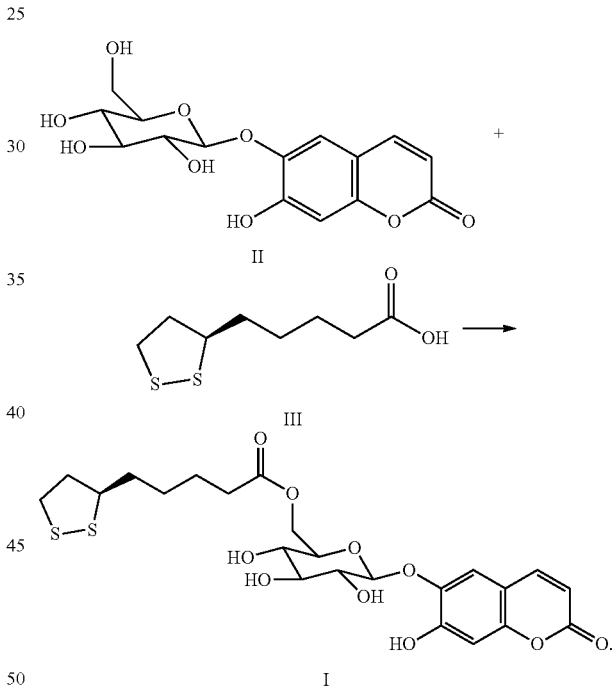

In another embodiment, the reaction of the compound of formula II with the compound of formula III comprises the following steps: placing the compound of formula II and the compound of formula III, in a molar ratio of 1:1 to 1:1.3, in a reactor; adding an organic solvent, N,N'-dicyclohexylcarbodiimide (DCC), and a catalyst to obtain a reaction mixture; and heating the reaction mixture at 30-55° C. for 3-4 hours under sonication.

In another embodiment, the organic solvent is acetonitrile or THF.

In another embodiment, the organic solvent is acetonitrile.

In another embodiment, the catalyst is benzyltriethylammonium chloride or thionyl chloride.

In another embodiment, the catalyst is benzyltriethylammonium chloride.

In another embodiment, the molar ratio of the compound of formula II and the compound of formula III is 1:1.1.

In another embodiment, the reaction mixture is heated at 50° C.

In another embodiment, the reaction mixture is heated for 4 hours.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings:

FIG. 1 shows the scavenging activity of the sample and control solutions at different concentrations.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

Example 1

Preparation of the Aesculin Lipoic Acid Ester (the Compound of Formula I)

100 mg (0.29 mmol) aesculin and 66.6 mg (0.32 mmol) of lipoic acid were placed in a 100 mL reactor. 60 mL acetonitrile was added to form a reaction mixture. 61.9 mg (0.3 mmol) DCC and 3.5 mg thionyl chloride were then added to the reaction mixture. The reaction mixture was heated at 35° C. under sonication and nitrogen atmosphere for 4 hours. The reaction mixture was cooled down to room temperature, concentrated under reduced pressure, filtered, and dried with sodium sulfate. Solvent in the reaction mixture was then removed to obtain 137.9 mg the aesculin lipoic acid ester, a yield of 88.79%.

$^1$H-NMR (400 MHz, DMSO-d6) δ (ppm): 7.74 (1H, d), 6.87 (1H, s), 6.73 (1H, s), 5.90 (1H, d), 5.81 (1H, d), 5.31 (1H, s), 4.01-4.30 (3H, m), 3.89 (1H, t), 3.52 (3H, s), 3.39-3.50 (2H, m), 2.63-2.49 (3H, m), 2.30 (2H, t), 2.00-1.71 (4H, m), 1.53 (2H, q), 1.28 (2H, m); $^{13}$C-NMR (400 MHz, DMSO-d$_6$) δ (ppm): 173.4, 160.6, 148.6, 145.8, 143.0, 113.6, 111.0, 109.7, 102.7, 78.9, 76.3, 73.6, 71.5, 63.4, 40.7, 38.3, 34.0, 29.3, 28.1; MS (ESI) for (M+H)$^+$: 529.12

Example 2

Preparation of the Aesculin Lipoic Acid Ester 100 mg (0.29 mmol) aesculin and 66.6 mg (0.32 mmol) of lipoic acid were placed in a 100 mL reactor. 60 mL acetonitrile was added to form a reaction mixture. 61.9 mg (0.3 mmol) DCC and 6.7 mg benzyltriethylammonium chloride (TEBAC) were then added to the reaction mixture. The reaction mixture was heated at 45° C. under sonication and nitrogen atmosphere for 4 hours. The reaction mixture was cooled down to room temperature, concentrated under reduced pressure, filtered, and dried with sodium sulfate. Solvent in the reaction mixture was then removed to obtain 121.3 mg the aesculin lipoic acid ester, a yield of 78.14%.

Example 3

Preparation of the Aesculin Lipoic Acid Ester 100 mg (0.29 mmol) aesculin and 78.7 mg (0.38 mmol) of lipoic acid were placed in a 100 mL reactor. 60 mL acetonitrile was added to form a reaction mixture. 61.9 mg (0.3 mmol) DCC and 3.5 mg thionyl chloride were then added to the reaction mixture. The reaction mixture was heated at 55° C. under sonication and nitrogen atmosphere for 3 hours. The reaction mixture was cooled down to room temperature, concentrated under reduced pressure, filtered, and dried with sodium sulfate. Solvent in the reaction mixture was then removed to obtain 129.3 mg the aesculin lipoic acid ester, a yield of 83.26%.

Example 4

Preparation of the Aesculin Lipoic Acid Ester 100 mg (0.29 mmol) aesculin and 66.6 mg (0.32 mmol) of lipoic acid were placed in a 100 mL reactor. 60 mL acetonitrile was added to form a reaction mixture. 61.9 mg (0.3 mmol) DCC and 3.5 mg thionyl chloride were then added to the reaction mixture. The reaction mixture was heated at 30° C. under sonication and nitrogen atmosphere for 3 hours. The reaction mixture was cooled down to room temperature, concentrated under reduced pressure, filtered, and dried with sodium sulfate. Solvent in the reaction mixture was then removed to obtain 124.4 mg the aesculin lipoic acid ester, a yield of 80.11%.

Example 5

Preparation of the Aesculin Lipoic Acid Ester 100 mg (0.29 mmol) aesculin and 66.6 mg (0.32 mmol) of lipoic acid were placed in a 100 mL reactor. 60 mL acetonitrile was added to form a reaction mixture. 61.9 mg (0.3 mmol) DCC and 6.7 mg benzyltriethylammonium chloride (TEBAC) were then added to the reaction mixture. The reaction mixture was heated at 50° C. under sonication and nitrogen atmosphere for 4 hours. The reaction mixture was cooled down to room temperature, concentrated under reduced pressure, filtered, and dried with sodium sulfate. Solvent in the reaction mixture was then removed to obtain 130.9 mg the aesculin lipoic acid ester, a yield of 84.28%.

Example 6

The Antioxidant Activity of the Aesculin Lipoic Acid Ester Measured by a DPPH Radical Scavenging Activity Assay 2,2-Diphenyl-1-picryl hydrazyl (DPPH) is an organic compound composed of a stable organic radical. In the DPPH molecule, due to the presence of multiple electron-withdrawing —NO$_2$ and large π bonds of the benzene ring, nitrogen free radical is stabilized. Its methanol solution is purple and has a maximum absorption peak at 517 nm. After the addition of an antioxidant, DPPH captures an electron to be paired with the free electron, and the purple fades and turns into a yellow substance. The absorption at 517 nm disappears, and the degree of fading is quantitatively related to the number of electrons it captures. Based on this principle, a spectrophotometer is used to detect the change of the absorbance of the DPPH radical and the sample solution, and the ability of the sample to provide hydrogen atoms and scavenge free radicals can be measured.

Preparation of DPPH solution: measuring exact amount of 2,2-diphenyl-1-picryl hydrazyl (DPPH) and dissolving in methanol to prepare a 0.2 mmol/L DPPH solution, stored at 0° C. in dark.

Preparation of sample solutions: the aesculin lipoic acid ester was diluted with a concentration gradient of 1.82, 7.28, 24.2, 48.4, 72.6, 96.8, 242, 484, 726, 968 ppm with acetonitrile to prepare sample solutions to be tested. Control samples (vitamin C, aesculin, lipoic acid, a mixture of aesculin and lipoic acid) were diluted with methanol in the same manner in the same concentration gradient to obtain the corresponding four groups of control solutions.

Specific Steps:

Measuring the Scavenging Activity of the Sample Solutions:

2 mL of the sample solutions at each concentration gradient was taken, 2 mL 0.2 mmol/L DPPH solution was added, the mixture was mixed and reacted at room temperature in dark for 30 minutes, and methanol was then added to adjust final volume. The absorbance $A_i$ was measured at 517 nm. 2 mL control solution and 2 mL methanol were mixed, and the absorbance $A_j$ was measured. 2 mL DPPH solution and 2 mL methanol were mixed, and the absorbance $A_0$ was measured. The scavenging activity of the sample solution and control solutions is calculated according to the following calculation formula.

Scavenging activity (%)=$100 \times [1-(A_i-A_j)/A_0]$

The scavenging activity is shown in Table 1 and FIG. 1. In FIG. 1, the X axis represents the concentrations (PPM) of the sample and control solutions, and the Y axis represents the scavenging activity.

The test results show that the antioxidant activity the aesculin lipoic acid ester is similar that of vitamin C, and the free radical clearance rate of more than 90% can be achieved at a lower concentration, which is significantly higher than those of aesculin, lipoic acid, and the mixture of aesculin and lipoic acid. The aesculin lipoic acid ester can be used a food and cosmetic antioxidant additive, and has a wide application prospect.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A compound having the following formula I:

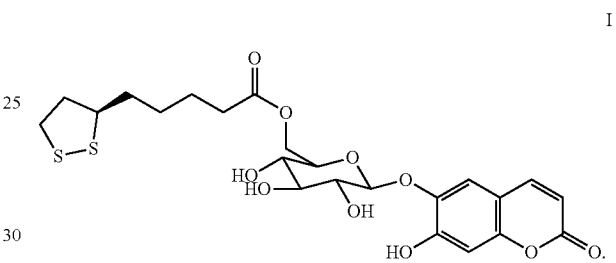

2. A method of preparing the compound of claim 1, comprising:
reacting the compound of formula II with the compound of formula III to obtain the compound of formula I:

TABLE 1

| Sample and Controls | Absorbance | Concentrations (ppm) | | | | | | | | | |
|---|---|---|---|---|---|---|---|---|---|---|---|
| | | 1.82 | 7.28 | 24.2 | 48.4 | 72.6 | 96.8 | 242 | 484 | 726 | 968 |
| Aesculin lipoic acid ester | $A_i$ | 0.652 | 0.543 | 0.405 | 0.269 | 0.172 | 0.114 | 0.143 | 0.052 | 0.049 | 0.049 |
| | $A_j$ | 0.020 | 0.019 | 0.018 | 0.021 | 0.021 | 0.020 | 0.020 | 0.020 | 0.021 | 0.020 |
| | $A_0$ | 0.915 | | | | | | | | | |
| | Scavenging activity (%) | 30.93 | 42.73 | 57.70 | 72.90 | 83.5 | 89.73 | 95.30 | 96.50 | 96.83 | 96.94 |
| Vitamin C | $A_i$ | 0.788 | 0.286 | 0.037 | 0.034 | 0.029 | 0.027 | 0.027 | 0.023 | 0.024 | 0.023 |
| | $A_j$ | 0.300 | 0.002 | 0.003 | 0.003 | 0.004 | 0.004 | 0.004 | 0.003 | 0.004 | 0.003 |
| | $A_0$ | 1.031 | | | | | | | | | |
| | Scavenging activity (%) | 23.86 | 72.45 | 96.70 | 96.99 | 97.58 | 97.77 | 97.77 | 98.06 | 98.06 | 98.06 |
| Aesculin | $A_i$ | 1.117 | 1.116 | 1.098 | 1.093 | 1.063 | 1.033 | 0.885 | 0.678 | 0.499 | 0.359 |
| | $A_j$ | 0.023 | 0.023 | 0.023 | 0.023 | 0.022 | 0.022 | 0.024 | 0.027 | 0.027 | 0.027 |
| | $A_0$ | 1.133 | | | | | | | | | |
| | Scavenging activity (%) | 3.44 | 3.53 | 5.12 | 5.56 | 8.12 | 10.77 | 24.01 | 42.54 | 58.34 | 70.70 |
| Lipoic acid | $A_i$ | 1.044 | 1.042 | 1.039 | 1.036 | 1.028 | 1.014 | 0.965 | 0.879 | 0.841 | 0.823 |
| | $A_j$ | 0.002 | 0.003 | 0.003 | 0.002 | 0.003 | 0.003 | 0.003 | 0.002 | 0.002 | 0.002 |
| | $A_0$ | 1.051 | | | | | | | | | |
| | Scavenging activity (%) | 0.86 | 1.14 | 1.43 | 1.62 | 2.47 | 3.81 | 8.47 | 16.65 | 20.17 | 21.88 |
| Mixture of aesculin and lipoic acid (1:1) | $A_i$ | 1.013 | 1.012 | 0.996 | 0.962 | 0.941 | 0.921 | 0.833 | 0.655 | 0.489 | 0.348 |
| | $A_j$ | 0.002 | 0.003 | 0.003 | 0.003 | 0.003 | 0.002 | 0.002 | 0.002 | 0.001 | 0.002 |
| | $A_0$ | 1.020 | | | | | | | | | |
| | Scavenging activity (%) | 0 88 | 1.08 | 2.65 | 5.98 | 8.04 | 9.90 | 18.53 | 35.98 | 52.16 | 66.08 |

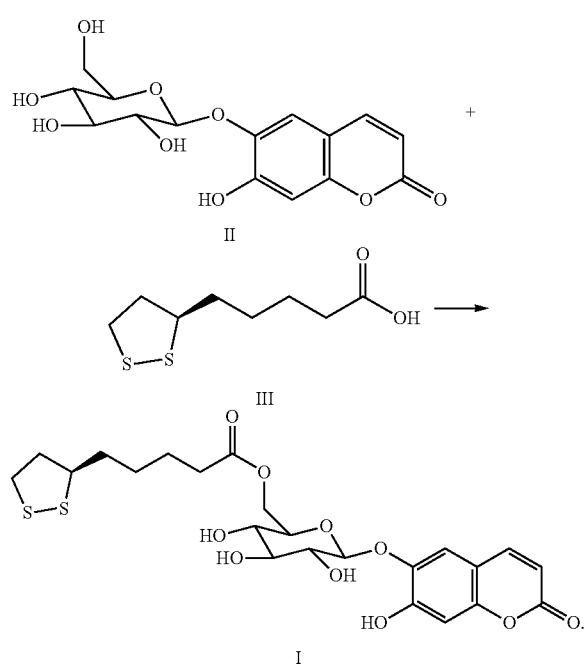

3. The method of claim 2, wherein the reaction of the compound of formula II with the compound of formula III comprises the following steps:
   placing the compound of formula II and the compound of formula III, in a molar ratio of 1:1 to 1:1.3, in a reactor;
   adding an organic solvent, N,N'-dicyclohexylcarbodiimide, and a catalyst to obtain a reaction mixture; and
   heating the reaction mixture at 30-55° C. for 3-4 hours under sonication.

4. The method of claim 3, wherein the organic solvent is acetonitrile or THF.

5. The method of claim 4, wherein the organic solvent is acetonitrile.

6. The method of claim 3, wherein the catalyst is benzyltriethylammonium chloride or thionyl chloride.

7. The method of claim 6, wherein the catalyst is benzyltriethylammonium chloride.

8. The method of claim 3, wherein the molar ratio of the compound of formula II and the compound of formula III is 1:1.1.

9. The method of claim 3, wherein the reaction mixture is heated at 50° C.

10. The method of claim 3, wherein the reaction mixture is heated for 4 hours.

* * * * *